United States Patent [19]

Friebe et al.

[11] Patent Number: 4,853,386

[45] Date of Patent: Aug. 1, 1989

[54] N6-DISUBSTITUTED PURINE DERIVATIVES, AND PHARMACEUTICAL COMPOSITIONS CONTAINING THEM, USEFUL FOR TREATING ALLERGIC DISEASES, BRONCHOSPASTIC AND BRONCHOCONSTRICTORY CONDITIONS

[75] Inventors: Walter-Gunar Friebe, Mannheim; Otto-Henning Wilhelms, Weinheim-Rittenweier, both of Fed. Rep. of Germany

[73] Assignee: Boehringer Mannheim GmbH, Mannheim, Fed. Rep. of Germany

[21] Appl. No.: 897,109

[22] Filed: Aug. 15, 1986

[30] Foreign Application Priority Data

Aug. 17, 1985 [DE] Fed. Rep. of Germany ....... 3529497

[51] Int. Cl.⁴ .................... A61K 31/52; C07D 473/34; C07D 473/16; C07D 473/40
[52] U.S. Cl. ................................. 514/266; 514/261; 544/277
[58] Field of Search ................. 544/277; 514/261, 266

[56] References Cited

U.S. PATENT DOCUMENTS

| | | | |
|---|---|---|---|
| 2,691,654 | 10/1954 | Hitchings et al. | 544/277 X |
| 3,016,378 | 1/1962 | Roch | 544/277 X |
| 3,813,394 | 5/1974 | Tensho et al. | 544/277 |
| 4,086,347 | 4/1978 | Friebe et al. | 514/266 |
| 4,212,866 | 7/1980 | Friebe et al. | 514/266 |
| 4,241,063 | 12/1980 | Naito et al. | 544/277 X |
| 4,294,831 | 10/1981 | Schaeffer | 514/261 |
| 4,609,661 | 9/1986 | Verheyden et al. | 514/262 |
| 4,612,314 | 9/1986 | Verheyden et al. | 514/261 |

FOREIGN PATENT DOCUMENTS

| | | | |
|---|---|---|---|
| 0552947 | 2/1958 | Canada | 544/277 |
| 0778787 | 2/1968 | Canada | 544/277 |
| 0138683 | 4/1985 | European Pat. Off. | 514/261 |
| 2249027 | 4/1973 | Fed. Rep. of Germany | 514/261 |
| 0006616 | 1/1985 | Japan | 514/261 |

OTHER PUBLICATIONS

Robins, et al., J. Am. Chem. Soc., vol. 83, pp. 2574–2579 (06/05/61).
Lister, et al., Chemical Abstracts, vol. 54:9935f–9936f (1960).
Lewis, et al., Chemical Abstracts, vol. 56:11588f–11589g (1962).
Baker, et al., Chemical Abstracts, vol. 60:4402g–4403g (1960).
Baker, et al., Chemical Abstracts, vol. 63:16350g (1965).
Schaeffer, et al., Chemical Abstracts, vol. 64:3911d (1966).
Hillers, et al., Chemical Abstracts, vol. 85:46563u (1976).
Hasan, et al., Chemical Abstracts, vol. 107:115913v (1987).

Primary Examiner—Anton H. Sutto
Assistant Examiner—Diana G. Rivers
Attorney, Agent, or Firm—Felfe & Lynch

[57] ABSTRACT

The present invention provides N6-disubstituted purine derivatives of the general formula:

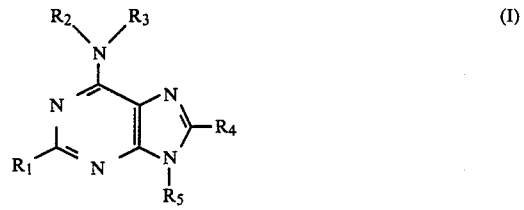

wherein $R_1$ and $R_4$ are the same or different and each represents a hydrogen or halogen atom or an $-NR_6R_7$ group, $R_2$ and $R_3$ are the same or different and each represents a $C_1-C_6$ alkyl radical, a $C_2-C_6$ alkenyl radical, a $C_3-C_7$ cycloalkyl radical, a phenalkyl radical containing up to 4 carbon atoms in the alkyl moiety, which can be straight-chained or branched, the phenyl moiety of which can be substituted one or more times by halogen, hydroxyl, $C_1-C_6$ alkyl, $C_1-C_6$ alkoxy, $C_1-C_6$ alkylthio or trifluoromethyl; a furylmethyl or furylethyl radical, a thiophenemethyl or thiopheneethyl radical, a pyridylmethyl or pyridylethyl radical optionally substituted by a $C_1-C_4$ alkyl radical, an indanyl radical or a tetrahydronaphthyl radical, $R_5$ is a hydrogen atom, a tetrahydrofuranyl or tetrahydropyranyl radical or a $C_1-C_{10}$ radical which is optionally substituted one or more times by hydroxyl, $C_1-C_6$ alkanoyloxy, $C_1-C_6$ alkoxycarbonyl, $C_2-C_6$ carboxyalkanoyloxy, $C_2-C_6$ hydroxyalkoxy, $C_3-c_6$ dihydroxyalkoxy, carboxyl, cyano or 1H-tetrazol-5-yl radical, $R_6$ and $R_7$ are the same or different and each represents a hydrogen atom or a $C_1-C_6$ alkyl radical or together represent a $C_2-C_5$ alkylene radical optionally interrupted by oxygen, sulphur or an $NR_8$ group and $R_8$ is a hydrogen atom or a $C_1-C_6$ alkyl radical; as well as the pharmacologically acceptable salts thereof.

26 Claims, No Drawings

N6-DISUBSTITUTED PURINE DERIVATIVES, AND PHARMACEUTICAL COMPOSITIONS CONTAINING THEM, USEFUL FOR TREATING ALLERGIC DISEASES, BRONCHOSPASTIC AND BRONCHOCONSTRICTORY CONDITIONS

The present invention is concerned with new $N^6$-disubstituted purine derivatives, processes for the preparation thereof and pharmaceutical compositions containing them.

The compounds according to the present invention can inhibit the antigen-caused SRS-A liberation from lung tissue samples. Therefore, they are suitable for the treatment of allergic diseases, as well as of bronchospastic and bronchoconstrictory reactions caused by inflammation.

The new $N^6$-disubstituted purine derivatives according to the present invention are compounds of the formula:

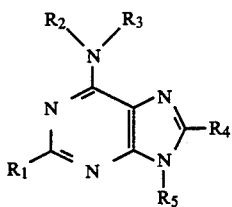

wherein $R_1$ and $R_4$ are the same or different and each represents a hydrogen or halogen atom or an $-NR_6R_7$ group, $R_2$ and $R_3$ are the same or different and each represents a $C_1-C_6$ alkyl radical, a $C_2-C_6$ alkenyl radical, a $C_3-C_7$ cycloalkyl radical, a phenalkyl radical containing up to 4 carbon atoms in the alkyl moiety, which can be straight-chained or branched, the phenyl moiety of which can be substituted one or more times by halogen, hydroxyl, $C_1-C_4$ alkyl, $C_1-C_6$ alkoxy, $C_1-C_6$ alkylthio or trifluoromethyl; a furylmethyl or furylethyl radical, a thiophenemethyl or thiopheneethyl radical, a pyridylmethyl or pyridylethyl radical optionally substituted by a $C_1-C_4$ alkyl radical, an indanyl radical or a tetrahydronaphthyl radical, $R_5$ is a hydrogen atom or a tetrahydrofuranyl or tetrahydropyranyl radical or a $C_1-C_{10}$ alkyl radical, which is optionally substituted one or more times by hydroxyl, $C_1-C_6$ alkanoyloxy, $C_1-C_6$ alkoxycarbonyl, $C_2-C_6$ carboxyalkanoyloxy, $C_2-C_6$ hydroxyalkoxy, $C_3-C_6$ dihydroxyalkoxy, carboxyl, cyano or 1H-tetrazol-5-yl, $R_6$ and $R_7$ are the same or different and each represents a hydrogen atom or a $C_1-C_6$ alkyl radical or together can represent a $C_2-C_5$ alkylene radical optionally interrupted by oxygen, sulphur or an $NR_8$ group and $R_8$ is a hydrogen atom or a $C_1-C_6$ alkyl radical; as well as the pharmacologically acceptable salts thereof.

The present invention also provides pharmaceutical compositions containing at least one compound of general formula (I), as well as therapeutic use of these.

The alkyl radicals in the above-mentioned substituents as well as the alkenyl, the alkoxy and the alkylthio radicals, can be straight-chained or branched. Preferred alkyl radicals include the methyl, ethyl, n-propyl, isopropyl, n-butyl, isobutyl, n-pentyl and 3-pentyl radicals. The alkenyl radical is preferably an allyl radical.

Alkoxy and alkylthio radicals are preferably the methoxy, ethoxy, methylthio and ethylthio radicals.

The phenalkyl radical can be, for example, a benzyl, phenethyl, phenylpropyl, phenylisopropyl or 3-methyl-3-phenylpropyl radical.

The substituent $R_5$ can be, in particular, a hydrogen atom or a tetrahydrofurn-2-yl, tetrahydropyran-2-yl, 2-hydroxypropyl, 2,3-dihydroxypropyl, 2-acetoxypropyl, 2-succinoyloxypropyl, (2-hydroxyethoxy)-methyl, 1-(1,3-dihydroxy-2-propoxy)-2-hydroxyethyl, 8-methoxycarbonylcoctyl, 8-carboxyoctyl, 4-cyanobutyl or 4-(1H-tetrazol-5-yl)-butyl radical.

Halogen atoms are preferably fluorine, chlorine or bromine atoms.

Apart from the compounds mentioned hereinafter in the Examples, the subject of the present invention is, in particular, all compounds which contain every possible combination of the substituents mentioned in the Examples.

The present invention also provides a process for the preparation of compounds of general formula (I), wherein a compound of the general formula:

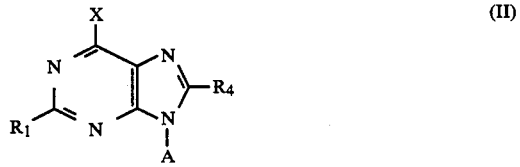

in which $R_1$ and $R_4$ have the above-mentioned meanings, X is a reactive residue and A stands for the above-mentioned substituent $R_5$ or is a ribofuranosyl radical, is reacted with a compound of the general formula:

$$R_2\text{-NH-}R_3 \quad (III)$$

in which $R_2$ and $R_3$ have the above-mentioned meanings, and subsequently, if desired, a ribofuranosyl radical A is converted into or replaced by a substituent $R_5$; a hydroxyl group contained in $R_5$ is liberated by splitting off a protective group; a hydroxyl group in $R_5$ is esterified by reaction with a reactive carboxylic acid derivative; an alkoxycarbonyl group contained in $R_5$ is saponified to give a carboxyl group; a cyano group contained in $R_5$ is converted with hydrazoic acid into a 1H-tetrazol-5-yl radical; a tetrahydrofuranyl or tetrahydropyranyl radical is replaced by a hydrogen atom; a hydrogen atom $R_5$ is replaced by another radical $R_5$ given in the definition of $R_5$; a substituent $R_1$ or $R_4$ is converted into another substituent given in the definitions of $R_1$ and $R_4$; and the compound obtained of general formula (I) is, if desired, converted into a pharmacologically acceptable salt by neutralization with a non-toxic acid.

The reactive residue X can be, for example, a chlorine or bromine atom or a lower alkylthio radical.

The conversion of a ribofuranosyl radical A into a substituent $R_5$ can take place, for example, by treatment with sodium metaperiodate and subsequent reduction with sodium tetrahydridoboranate.

Furthermore, a ribofuranosyl radical can be split off by treatment with a mineral acid and the product obtained, in which $R_5$ is a hydrogen atom, converted by alkylation into a compound of general formula (I) in which $R_5$ is other than a hydrogen atom.

Depending upon its nature, the splitting off of a hydroxyl protective group can take place either in the case of an alkanoyl or aroyl radical by acidic or alkaline saponification or in the case of a benzyl protective group by hydrogenolysis or treatment with a mineral acid or in the case of a ketal protective group by acid hydrolysis.

For the esterification of hydroxyl groups, there can be used, for example, carboxylic acids or derivatives thereof, such as carboxylic acid halides or anhydrides, carboxylic acid azides or activated esters.

The reaction of a cyano group with hydrazoic acid preferably takes place by production of the latter in situ, for example from an alkali metal azide and ammonium chloride.

For the splitting off of a tetrahydrofuranyl or tetrahydropyranyl radical, there can be used inorganic acids, such as hydrochloric acid or sulphuric acid, in aqueous or organic solution.

A conversion of a compound of general formula (I), in which $R_5$ is a hydrogen atom, into a compound of general formula (I), in which $R_5$ is other than a hydrogen atom, preferably takes place by alkylation with a compound of the general formula $R_5$-Y, wherein Y is a reactive residue, for example halogen, methanesulphonyloxy or toluenesulphonyloxy, in an acid-binding medium.

A conversion of a substituent $R_1$ or $R_4$ into another substituent of the above-given definitions of $R_1$ and $R_4$ can take place, for example, by replacing a hydrogen atom by halogenation, replacing a halogen atom by amination or exchanging an amino function by a halogen atom by reaction with a nitrosyl halide.

The starting compounds of general formulae (II) and (III) are either known from the literature or can be prepared analogously to processes known from the literature.

The pharmacologically acceptable salts are obtained in the usual way, for example by neutralization of compounds of general formula (I) with non-toxic or organic acids, for example hydrochloric acid, sulphuric acid, phosphoric acid, hydrobromic acid, acetic acid, lactic acid, citric acid, malic acid, salicylic acid, malonic acid, maleic acid or succinic acid.

For the preparation of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvants, are suspended or dissolved in water or in an oil, for example olive oil.

The compounds of general formula (I) can be administered orally or parenterally in liquid or solid form. As injection medium, it is preferred to use water which contains the stabilizing agents, solubilizing agents and/or buffers usual in the case of injection solutions. Additives of this kind include, for example, tartrate and borate buffers, ethanol, dimethyl sulphoxide, complex formers (such as ethylenediamine-tetraacetic acid), high molecular weight polymers (such as liquid polyethylene oxide) for viscosity regulation or polyethylene derivatives or sorbitan anhydrides.

Solid carrier materials include, for example, starch, lactose, mannitol, methyl cellulose, talc, highly dispersed silicic acids and high molecular weight polymers (such as polyethylene glycols).

Compositions suitable for oral administration can, if desired, contain flavouring and sweetening agents. For external use, the compounds of general formula (I) according to the present invention can also be used in the form of powders and salves. For this purpose, they are mixed, for example, with powdered, physiologically acceptable dilution agents or with conventional salve bases.

The dosage administered depends upon the age, the state of health and the weight of the recipient, the extent of the disease, the nature of further treatments possibly carried out simultaneously, the frequency of the treatment and the nature of the desired action. Usually, the daily dosage of the active compound is 0.1 to 50 mg./kg. of body weight. Normally, 0.5 to 40 and preferably 1.0 to 20 mg./kg./day in one or more administrations per day are effective for obtaining the desired results.

The following Examples are given for the purpose of illustrating the present invention:

EXAMPLE 1

6-[Benzyl-N-(2-methylpropyl)-amino]-9-tetrahydropyran-2-yl purine

A mixture of 10.7 g. (40 mmole) 6-chloro-9-tetrahydropyran-2-yl purine, 19.5 g. (120 mmole) N-benzyl--methylpropylamine and 60 ml. butanol is heated under reflux for 16 hours. The reaction mixture is evaporated and the residue is taken up in dichloromethane, washed with dilute acetic acid and subsequently with water, dried over anhydrous sodium sulphate, evaporated and the residue triturated with ligroin. There are obtained 14.2 g. of the title compound (97% of theory); m.p. 93°–95° C.

EXAMPLE 2

The following compounds are obtained in a manner analogous to that described in Example 1:

| designation | yield (%) | melting point °C. (solvent) |
| --- | --- | --- |
| (a) 6-[N—(5-chloro-2-methoxy)-benzyl-N—cyclopentylamino]-9-tetrahydropyran-2-ylpurine from 6-chloro-9-tetrahydropyran-2-ylpurine and N—(5-chloro-2-methoxy)-benzylcyclopentylamine | 75 | 142–144 (ligroin) |
| (b) 6-[N—cyclopentyl-N—(furan-2-yl-methyl)-amino]-9-tetrahydropyran-2-yl-purine from 6-chloro-9-tetrahydropyran-2-yl-purine and N—cyclopentyl-(furan-2-yl-methyl)-amine | 85 | hydrochloride 143–144 (diethyl ether) |
| (c) 6-(N—allyl-N—cyclohexyl-amino)-9-tetrahydrofuran-2-yl-purine from 6-chloro-9-tetrahydrofuran-2-yl-purine and N—allyl-cyclohexylamine | 54 | oil (dichloromethane) |
| (d) 6-(N—allyl-N—cyclohexyl-amino)-9-tetrahydropyran-2-yl-purine from 6-chloro-9-tetrahydropyran-2-yl-purine and N—allyl-cyclohexylamine | 69 | 77–78 (hexane) |
| (e) 6-[N—cyclopentyl-N—(3-trifluoromethylbenzyl)-amino]-9-tetrahydropyran-2-yl-purine from 6-chloro-9-tetrahydropyran-2-yl-purine and N—cyclopentyl-(3-trifluoromethylbenzyl)-amine | 52 | 112–113 (ligroin) |
| (f) 6-(N—benzyl-N—cyclopentyl-amino)-9-tetrahydrofuran-2-yl-purine from | 67 | 88–90 (hexane) |

| designation | yield (%) | melting point °C. (solvent) |
|---|---|---|
| 6-chloro-9-tetrahydrofuran-2-yl-purine and N—benzyl-cyclopentylamine | | |
| (g) 6-(N—benzyl-N—cyclopentyl-amino)-9-tetrahydropyran-2-yl-purine from 6-chloro-9-tetrahydropyran-2-yl-purine and N—benzyl-cyclopentylamine | 71 | 91–93 (hexane) |
| (h) 6-[N—cyclopentyl-N—(4-methoxybenzyl)-amino]-9-tetrahydrofuran-2-yl-purine from 6-chloro-9-tetrahydrofuran-2-yl-purine and N—cyclopentyl-(4-methoxybenzyl)-amine | 83 | 74–76 (hexane) |
| (i) 6-[N—(cyclopentyl-N—(4-methoxybenzyl)-amino]-9-tetrahydropyran-2-yl-purine from 6-chloro-9-tetrahydropyran-2-purine and N—cyclopentyl-(4-methoxybenzyl)-amine | 66 | 97–99 (ligroin) |
| (j) 6-[N—cyclopentyl-N—(2,5-dimethylbenzyl)-amino]-9-tetrahydrofuran-2-yl-purine from 6-chloro-9-tetrahydrofuran-2-yl-purine and N—cyclopentyl-(2,5-dimethylbenzyl)-amine | 48 | oil (dichloromethane) |
| (k) 6-[N—cyclopentyl-N—(2,5-dimethylbenzyl)-amino]-9-tetrahydropyran-2-yl-purine from 6-chloro-9-tetrahydropyran-2-yl-purine and N—cyclopentyl-(2,5-dimethylbenzyl)-amine | 51 | 103–105 (ligroin) |
| (l) 6-[N—cyclopentyl-N—(thiophen-2-yl-methyl)-amino]-9-tetrahydrofuran-2-yl-purine from 6-chloro-9-tetrahydrofuran-2-yl-purine and N—cyclopentyl-(thiophen-2-yl-methyl)-amine | 56 | 62–64 (hexane) |
| (m) 6-[N—cyclopentyl-N—(thiophen-2-yl-methyl)-amino]-9-tetrahydropyran-2-yl-purine from 6-chloro-9-tetrahydropyran-2-yl-purine and N—cyclopentyl-(thiophen-2-yl-methyl)-amine | 79 | 74–76 (ligroin) |
| (n) 6-{N—(2-methylpropyl)-N—[2-(thiophen-2-yl)-ethyl]-amino}-9-tetrahydropyran-2-yl-purine from 6-chloro-9-tetrahydropyran-2-yl-purine and N—(2-methylpropyl)-[2-(thiophen-2-yl)-ethyl]-amine | 70 | oil (dichloromethane) |
| (o) 6-[N—(indan-1-yl)-N—(2-methylpropyl)-amino]-9-tetrahydropyran-2-yl-purine from 6-chloro-9-tetrahydropyran-2-yl-purine and N—(indan-1-yl)-(2-methylpropyl)-amine | 63 | 108–110 (ligroin) |
| (p) 6-[N—cyclopentyl-N—(4-methylbenzyl)-amino]-9-tetrahydropyran-2-yl-purine from 6-chloro-9-tetrahydropyran-2-yl-purine and N—cyclopentyl-(4-methylbenzyl)-amine | 92 | oil (dichloromethane) |
| (q) 6-[N—(4-chlorobenzyl)-N—(3-pentyl)-amino]-9-tetrahydropyran-2-yl-purine from 6-chloro-9-tetrahydropyran-2-yl-purine and N—(4-chlorobenzyl)-3-pentylamine | 77 | oil (dichloromethane) |
| (r) 6-[N—allyl-N—(indan-1-yl)-amino]-9-tetrahydropyran-2-yl-purine from 6-chloro-9-tetrahydropyran-2-yl-purine and N—allyl-indan-1-yl-amine | 75 | hydrochloride 155–160 (diethyl ether) |
| (s) 6-[N—(4-methoxybenzyl)-N—(3-pentyl)-amino]-9-tetrahydropyran-2-yl-purine from 6-chloro-9-tetrahydropyran-2-yl-purine and N—(4-methoxybenzyl)-3-pentylamine | 86 | 115–118 (diethyl ether) |
| (t) 6-[N—cyclopentyl-N—(2-methylbenzyl)-amino]-9-tetrahydropyran-2-yl-purine from 6-chloro-9-tetrahydropyran-2-yl-purine and N—cyclopentyl-(2-methylbenzyl)-amine | 90 | oil (diethyl ether) |
| (u) 6-[N—cyclopentyl-N—(pyridin-2-yl-methyl)-amino]-tetrahydropyran-2-yl-purine from 6-chloro-9-tetrahydropyran-2-yl-purine and N—cyclopentyl-N—(pyridin-2-yl-methyl)-amine | 62 | oil (dichloromethane) |
| (v) 6-[N—cyclopentyl-N—(2-methylpyridin-6-yl-methyl)-amino]-9-tetrahydropyran-2-yl-purine from 6-chloro-9-tetrahydropyran-2-yl-purine and N—cyclopentyl-N—(2-methylpyridin-6-yl-methyl)-amine | 66 | 126–129 (diethyl ether) |

EXAMPLE 3

6-[N-Cyclopentyl-N-(2,5-dimethylbenzyl)-amino]-9-[(2-hydroxyethoxy)-methyl]-purine hydrochloride A mixture of 9.0 g. (27 mmole) 9-[(2-benzoyloxyethoxy)-methyl]-6-chloropurine, 16.5 g. (81 mmole) N-cyclopentyl-(2,5-dimethylbenzyl)-amine and 130 ml. butanol is heated under reflux for 16 hours. The reaction mixture is evaporated, the residue is taken up in dichloromethane, washed with dilute acetic acid and subsequently with water, dried over anhydrous sodium sulphate, evaporated, mixed with a solution of 3.3 g. sodium in 200 ml. methanol, heated under reflux for 3 hours, evaporated and the residue taken up in water, extracted with dichloromethane, dried over anhydrous sodium sulphate and evaporated. After chromatography on silica gel with an elution mixture of 95% dichloromethane and 5% methanol, there are obtained 8.0 g. of the title compound (75% of theory) in the form of an oily base, the hydrochloride of which, prepared in ethyl acetate, melts at 132°–135° C.

EXAMPLE 4

In a manner analogous to that described in Example 3, there is obtained 6-[N-cyclopentyl-N-(thiophen-2-ylmethyl)-amino]-9-[(2-hydroxyethoxy)-methyl]-purine in a yield of 78% of theory in the form of an oily base.

EXAMPLE 5

6-[N-Benzyl-N-(2-methylpropyl)-amino]-purine

A solution of 17.0 g. (47 mmole) 6-[N-benzyl-N-(2-methylpropyl)-amino]-9-tetrahydropyran-2-ylpurine (compound of Example 1) in 200 ml. saturated ethanolic hydrogen chloride solution is heated under reflux for 10 minutes. After standing overnight, the reaction mixture is diluted with water, adjusted to pH 7 with aqueous ammonia solution and the precipitate filtered off with suction. After recrystallization from aqueous propan-2- ol, there are obtained 10.5 g. of the title compound (80% of theory); m.p. 160°–162° C.

EXAMPLE 6

The following compounds are obtained in a manner analogous to that described in Example 5:

| designation | yield (%) | melting point. °C. (solvent) |
|---|---|---|
| (a) 6-[N—cyclopentyl-N—(3-trifluoromethylbenzyl)-amino]-purine from the compound of Example 2e | 72 | 163–165 (propan-2-ol) |
| (b) 6-[N—(5-chloro-2-methoxy)-benzyl-N—cyclopentylamino]-purine from the compound of Example 2 a | 63 | 219–221 (propan-2-ol) |
| (c) 6-[N—cyclopentyl-N—(4-methylbenzyl)-amino]-purine from the compound of Example 2 p | 61 | 220–222 (water) |
| (d) 6-[N—(4-chlorobenzyl)-N—(3-pentyl)-amino]-purine from the compound of Example 2 q | 82 | 153–155 (ligroin) |
| (e) 6-{N—(2-methylpropyl)-N—[2-(thiophen-2-yl)-ethyl]-amino}-purine from the compound of Example 2 n | 85 | 115–117 (ligroin) |
| (f) 6-[N—(indan-1-yl)-N—(2-methylpropyl)-amino]-purine from the compound of Example 2 o | 43 | 86–88 (diethyl ether) |
| (g) 6-[N—allyl-N—(indan-1-yl)-amino]-purine from the compound of Example 2 r | 91 | hydrochloride 88–90 (ethanol) |
| (h) 6-[N—(4-methoxybenzyl)-N—(3-pentyl)-amino]-purine from the compound of Example 2 s | 53 | 152–155 (diethyl ether) |
| (i) 6-[N—cyclopentyl-N—(2-methylbenzyl)-amino]-purine from the compound of Example 2 t | 83 | 190–193 (water) |
| (j) 6-[N—cyclopentyl-N—(thiophen-2-ylmethyl)-amino]-purine from the compound of Example 2 m | 74 | 182–184 (diethyl ether) |
| (k) 6-[N—cyclopentyl-N—(4-methoxybenzyl)-amino]-purine from the compound of Example 2 i | 47 | 170–172 (water) |
| (l) 6-[N—cyclopentyl-N—(3-trifluoromethylbenzyl)-amino]-2-methylaminopurine from the compound of Example 23b | 39 | 80–90 (amorphous) (dichloromethane) |
| (m) 6-[N—cyclopentyl-N—(2,5-dimethylbenzyl)-amino]-2-methylaminopurine from 6-[N—cyclopentyl-N—(2,5-dimethylbenzyl)-amino]-2-methylamino-9-tetrahydropyran-2-yl-purine | 65 | 203–205 (propan-2-ol) |
| (n) 6-[N—cyclopentyl-N—(furan-2-ylmethyl)-amino]-2-methylaminopurine from the compound of Example 23 c | 53 | 162–163 (diethyl ether) |
| (o) 6-[N—cyclopentyl-N—(pyridin-2-ylmethyl)-amino]-purine from the compound of Example 2 u | 62 | 200–203 (diethyl ether) |

EXAMPLE 7

6-[N-Benzyl-N-(2-propyl)-amino]-purine

A solution of 3.5 g. (mmol) 6-[N-benzyl-N-(2-propyl)-amino]-9-ribofuranosylpurine and 50 ml. 2N hydrochloric acid is heated under reflux for 30 minutes. After cooling, it is washed with diethyl ether, the aqueous phase is adjusted to pH 7 with aqueous ammonia solution and the precipitate is recrystallized from aqueous propan-2-ol. There is obtained 1.8 g. of the title compound (75% of theory); m.p. 200°–202° C.

EXAMPLE 8

The following compounds are obtained in a manner analogous to that described in Example 7 from the appropriate 9-ribofuranosyl compounds:

| designation | yield (%) | melting point °C. (solvent) |
|---|---|---|
| (a) 6-[N—cyclohexyl-N—(2-methylpropyl)-amino]-purine | 72 | 152–153 (propan-2-ol) |
| (b) 6-(N—benzyl-N—cyclopentylamino)-purine | 91 | 232–233 (water) |
| (c) 6-[N—cyclopentyl-N—(4-fluorobenzyl)-amino]-purine | 82 | 236–238 (water) |
| (d) 6-[N—cyclopentyl-N—(furan-2-ylmethyl)-amino]-purine | 76 | 181–183 (diethyl ether) |
| (e) 6-[N—cyclopentyl-N—(thiophen-2-ylmethyl)-amino]-2-methylaminopurine | 63 | 180–182 (diethyl ether) |
| (f) 6-[N—cyclopentyl-N—(thiophen-2-ylmethyl)-amino]-2-dimethylaminopurine | 65 | 204–206 (diethyl ether) |
| (g) 6-(N—allyl-N—cyclohexylamino)-2-methylaminopurine | 56 | 160–162 (diethyl ether) |
| (h) 6-(N—allyl-N—cyclohexylamino)-2-dimethylaminopurine | 69 | 175–177 (water) |
| (i) 6-(N—allyl-N—cyclohexylamino)-8-dimethylaminopurine | 60 | 165–167 (propan-2-ol) |
| (j) 6-(N—allyl-N—cyclohexylamino)-purine | 94 | 132–133 (water) |
| (k) 6-[N—cyclopentyl-N—(2,5-dimethylbenzyl)-amino]-purine | 79 | 229–231 (methanol) |
| (l) 6-[N—cyclopentyl-N—(6-methylpyridin-2-ylmethyl)-amino]-purine | 69 | 113–115 (water) |

EXAMPLE 9

6-(N-Allyl-N-cyclohexylamino)-9-[1-(1,3-dihydroxy-2-propoxy-2-hydroxyethyl]-purine To a solution of 3.9 g. (10 mmol) 6-(N-allyl-N-cyclohexylamino)-9-ribofuranosyl-purine in 100 ml. methanol is added dropwise at ambient temperature a solution of 2.1 g. sodium metaperiodate in 40 ml. water, stirred for 4 hours at ambient temperature, filtered and the filtrate evaporated. The residue is taken up in 100 ml. methanol, 20 ml. water are added thereto, mixed with 3.7 g. sodium tetrahydridoboranate, stirred for 2 hours at ambient temperature, evaporated, the residue taken up in dichloromethane, washed with water, dried and evaporated. There are obtained 2.9 g. of the title compound (74% of theory) as an amorphous powder; m.p. 60°–65° C.

EXAMPLE 10

In a manner analogous to that described in Example 9, the following compounds are obtained from the appropriate 9-ribofuranosyl compounds:

| designation | yield (%) | melting point °C. (solvent) |
|---|---|---|
| (a) 6-[N—cyclopentyl-N—(2,5-dimethylbenzyl)-amino]-9-[1-(1,3-dihydroxy-2-propoxy)-2-hydroxyethyl]-purine | 70 | 80–86 (dichloromethane) |
| (b) 6-(N—benzyl-N—cyclopentyl- | 72 | 55–60 |

| designation | yield (%) | melting point °C. (solvent) |
|---|---|---|
| amino)-9-[1-(1,3-dihydroxy-2-propoxy)-2-hydroxyethyl]-purine | | (dichloromethane) |
| (c) 6-[N—cyclopentyl-N—(4-methoxybenzyl)-amino]-9-[1-(1,3-dihydroxy-2-propoxy)-2-hydroxyethyl]-purine | 88 | 70–80 (ethyl acetate) |
| (d) 6-[N—cyclopentyl-N—(thiophen-2-ylmethyl)-amino]-9-[1-(1,3-dihydroxy-2-propoxy)-2-hydroxyethyl]-purine | 62 | 50–55 (ethyl acetate) |

EXAMPLE 11

6-[N-Benzyl-N-(2-ethylpropyl)-amino]-9-(2,3-dihydroxypropyl)-purine

To a mixture of 1.44 g. (30 mmole) 50% sodium hydride in 100 ml. dimethylformamide is added dropwise a solution of 8.4 g. (30 mmole) 6-[N-benyzl-N-(2-methylpropyl)-amino]-amino]-purine (compound of Example 5) in 30 ml. dimethylformamide. The reaction mixture is stirred for 90 minutes at 80° C., a solution of 8.6 g. (30 mmole) 2,2-dimethyl-4-(4-methylbenzenesulphonyloxymethyl)-1,3-dioxalan is added dropwise thereto, stirring is continued for 1 hour at 80° C., the reaction mixture is evaporated and the residue is taken up in dichloromethane, washed with water, dried and evaporated. The residue is taken up in 200 ml. 0.1 N hydrochloric acid, stirred for 8 hours at 80° C., cooled, washed with diethyl ether, rendered alkaline and extracted with dichloromethane. After drying and evaporating, the residue is chromatographed on silica gel (elution agent: dichloromethane/methanol 95:5 v/v), the title compound being isolated as the hydrochloride. The yield is 5.2 g. (44% of theory); m.p. 155°–157° C., after recrystallization from diethyl ether.

EXAMPLE 12

The following compounds are obtained in a manner analogous to that described in Example 11:

| designation | yield (%) | melting point °C. (solvent) |
|---|---|---|
| (a) 6-[N—cyclopentyl-N—(2,5-dimethylbenzyl)-amino]-9-(2,3-dihydroxypropyl)-purine from the compound of Example 8 k | 38 | 70–73 (ligroin) |
| (b) 6-(N—benzyl-N—cyclopentyl-amino)-9-(2,3-dihydroxypropyl)-purine from the compound of Example 8 b | 55 | 133–135 (water) |
| (c) 6-[N—cyclopentyl-N—(4-methoxybenzyl)-amino]-9-(2,3-dihydroxypropyl)-purine from the compound of Example 6 k | 42 | 110–112 (diethyl ether) |
| (d) 6-[N—cyclopentyl-N—(thiophen-2-ylmethyl)-amino-9-(2,3-dihydroxypropyl)-purine | 33 | 108–110 (diethyl ether) |
| (e) 6-[N—cyclohexyl-N—(2-methylpropyl)-amino]-9-(2,3-dihydroxypropyl)-purine from the compound of Example 8 a | 47 | 60–80 amorphous (dichloromethane) |
| (f) 6-[N—cyclopentyl-N—(3-trifluoromethylbenzyl)-amino]-9-(2,3-dihydroxypropyl)-purine from the compound of Example 6 a | 52 | 60–70 amorphous (dichloromethane) |
| (g) 6-[N—(5-chloro-2-methoxybenzyl)-N—cyclopentylamino]-9-(2,3-dihydroxypropyl)-purine from the compound of Example 6 b | 44 | 60–70 amorphous (dichloromethane) |
| (h) 6-[N—cyclopentyl-N—(2-methylbenzyl)-amino]-9-(2,3-dihydroxypropyl)-purine from the compound of Example 6 i | 65 | hydrochloride 114–116 (diethyl ether) |
| (i) 6-[N—cyclopentyl-N—(4-methylbenzyl)-amino]-9-(2,3-dihydroxypropyl)-purine from the compound of Example 6 c | 45 | 158–160 (ethyl acetate) |
| (j) 6-[N—(indan-1-yl)-N—(2-methylpropyl)-amino]-9-(2,3-dihydroxypropyl)-purine from the compound of Example 6 f | 29 | oil (dichloromethane) |
| (k) 6-(N—allyl-N—cyclohexylamino)-9-(2,3-dihydroxypropyl)-purine from the compound of Example 8 j | 47 | hydrochloride 70–75 amorphous (diethyl ether) |
| (l) 6-(N—allyl-N—cyclohexylamino)-9-(2,3-dihydroxypropyl)-2-methylaminopurine from the compound of Example 8 g | 74 | 125–127 (diethyl ether) |
| (m) 6-[N—cyclopentyl-N—(2-methyl-pyridin-6-ylmethyl)-amino]-9-(2,3-dihydroxypropyl)-purine from 6-[N—cyclopentyl-N—(2-methylpyridin-6-ylmethyl)-amino]-purine | 54 | 139–140 (diethyl ether) |

EXAMPLE 13

6-(N-Allyl-N-cyclohexylamino)-9-(8-methoxycarbonyloctyl)-purine

To a solution of 0.7 g. (30 mmole) sodium in 100 ml. propan-2-ol are added 7.7 g. (30 mmole) 6-(N-allyl-N-cyclohexylamino)-purine (compound of Example 8 j), the reaction mixture is heated to 40° C. for 10 minutes, 7.5 g. (30 mmole) methyl 9-bromononanoate are added thereto, the reaction mixture is heated under reflux for 16 hours and evaporated and the residue is taken up in water, extracted with dichloromethane, dried and evaporated. After chromatography on silica gel (elution agent: dichloromethane/methanol 95:5 v/v), there are obtained 4.8 g. of the title compound (37% of theory) in the form of an oil.

EXAMPLE 14

6-(N-Allyl-N-cyclohexylamino)-9-(8-carboxyoctyl)-purine 3.2 g. (7.5 mmole) of the compound of Example 13 are heated under reflux for 5 hours with 50 ml. 5% aqueous sodium hydroxide solution and 40 ml. ethanol. The reaction mixture is evaporated and the residue is taken up in water, washed with diethyl ether and the aqueous phase is adjusted to pH 6, extracted with dichloromethane, dried and evaporated. After trituration of the residue with diethyl ether, there are obtained 2.2 g. of the title compound (71% of theory); m.p. 100°–102° C.

EXAMPLE 15

6-(N-Allyl-N-cyclohexylamino)-9-(2-hydroxypropyl)-purine

To a solution of 12.8 g. (50 mmole) 6-[N-allyl-N-cyclohexylamino)-purine (compound of Example 8 j) in 150 ml. dimethyl sulphoxide are added at 40° C. 7.6 g. potassium carbonate. The reaction mixture is stirred for 10 minutes, cooled to ambient temperature, 5.8 g. 1,2-epoxypropane are added dropwise thereto, the reaction mixture is stirred for 5 days at ambient temperature and evaporated and the residue chromatographed on silica gel (elution agent: dichloromethane/methanol 97:3 v/v). After trituration with diethyl ether, there are isolated 5.7 g. of the title compound )36% of theory); m.p. 108°-110° C.

EXAMPLE 16

6-(N-Allyl-N-cyclohexylamino)-9-(2-acetoxypropyl)-purine

To a solution of 2.3 g. (7.5 mmole) of the compound of Example 15 in 30 ml. pyridine there is added dropwise 1.0 ml. of acetic anhydride. The reaction mixture is stirred for 16 hours at ambient temperature, poured into water, extracted with ethyl acetate, washed neutral, dried and evaporated. There is obtained 1.8 g. of the title compound (67% of theory) in the form of an oil.

EXAMPLE 17

6-(N-Allyl-N-cyclohexylamino)-9-(2-succinoyloxy-propyl)-purine

To a solution of 3.0 g. (10 mmole) of the compound of Example 15 in 40 ml. pyridine is added 1.3 g. succinic anhydride and the reaction mixture is heated to 50° C. for 3 days, taken up in dichloromethane, washed with dilute acetic acid, evaporated and the residue is taken up in dilute aqueous sodium hydrogen carbonate solution, washed with diethyl ether and the aqueous phase adjusted to pH 5. There are isolated 2.4 g. of the title compound (58% of theory); m.p. 122°-123° C.

EXAMPLE 18

6-[N-Cyclopentyl-N-(2,5-dimethylbenzyl)-amino]-9-(4-cyanobutyl)-purine

To a solution of 0.34 g. sodium in 50 ml. propan-2-ol are added 4.8 g. (15 mmole) of the compound of Example 8k, the reaction mixture is heated under reflux for 10 minutes, 2.45 g. 5-bromovaleronitrile are added thereto and the reaction mixture is heated under reflux for 4 days. The reaction mixture is evaporated and the residue is taken up in dichloromethane, washed with water, evaporated and the residue chromatographed on silica gel. After elution with dichloromethane/methanol 97:3 v/v, there are obtained 3.8 g. of the title compound (63% of theory) in the form of an oil.

EXAMPLE 19

The following compounds are obtained in a manner analogous to that described in Example 18:

| designation | yield (%) | melting point °C. (solvent) |
| --- | --- | --- |
| (a) 6-[N—cyclopentyl-N—(furan-2-ylmethyl)-amino]-9-(4-cyanobutyl)-purine from the compound of Example 8 d | 57 | |
| (b) 6-[N—cyclopentyl-N—(thiophen-2-ylmethyl)-amino]-9-(4-cyanobutyl)-purine from the compound of Example 6 j | 46 | |

EXAMPLE 20

6-[N-Cyclopentyl-N-(2,5-dimethylbenzyl)-amino]-9-[4-(1H-tetrazol-5-yl)-butyl]-purine hydrochloride A mixture of 3.8 g. (9.4 mmole) of the compound of Example 18, 1.9 g. sodium azide, 1.5 g. ammonium chloride and 30 ml. dimethylformamide is heated to 125° C. for 3 days. A further 1.2 g. sodium azide and 1.0 g. ammonium chloride are added thereto, stirring is continued for 6 hours at 125° C., the reaction mixture is cooled and evaporated and the residue is taken up in ethyl acetate, washed with water, extracted with 1N aqueous sodium hydroxide solution and the aqueous phase is acidified with hydrochloric acid. After extraction with dichloromethane, evaporation and trituration of the residue with diethyl ether, there is obtained 1.7 g. of the title compound (38% of theory); m.p. 140°-142° C.

EXAMPLE 21

The following compounds are obtained in a manner analogous to that described in Example 20:

| designation | yield (%) | melting point °C. (solvent) |
| --- | --- | --- |
| (a) 6-[N—cyclopentyl-N—(furan-2-ylmethyl)-amino]-9-[4-(1H—tetrazol-5-yl)-butyl]-purine from the compound of Example 19 a | 53 | 113–115 (diethyl ether) |
| (b) 6-[N—cyclopentyl-N—(thiophen-2-ylmethyl)-amino]-9-[4-(1H—tetrazol-5-yl)-butyl]-purine from the compound of Example 19 b | 61 | 109–111 (diethyl ether) |

EXAMPLE 22

6-(N-Allyl-N-cyclohexylamino)-2-methylamino-9-tetrahydrofuran-2-ylpurine

A mixture of 8.5 g. (22 mmole) 6-(N-allyl-N-cyclohexylamino)-2-chloro-9-tetrahydrofuran-2-ylpurine and 150 ml. methanol, which has been saturated with methylamine, is heated to 100° C. in an autoclave for 48 hours. The reaction mixture is then evaporated, the residue is taken up in dichloromethane, washed with water, dried and evaporated. After chromatography with dichloromethane, there are obtained 6.4 g. of the title compound (82% of theory) in the form of an oil.

EXAMPLE 23

The following compounds are obtained in a manner analogous to that described in Example 22:

| designation | yield (%) | melting point °C. (solvent) |
| --- | --- | --- |
| (a) 6-(N—allyl-N—cyclohexylamino)-2-methylamino-9-tetrahydropyran-2-yl-purine from 6-(N—allyl-N—cyclohexylamino)-2-chloro-9-tetrahydropyran-2-yl-purine and methylamine | 67 | oil (dichloromethane) |
| (b) 6-[N—cyclopentyl-N—(3-trifluoromethylbenzyl)-amino]-2-methylamino-9-tetrahydropyran-2-yl-purine from 6-[N—cyclopentyl-N—(3-trifluoromethylbenzyl)-amino]-2-chloro-9-tetrahydropyran-2-ylpurine and | 61 | 133–135 (diethyl ether) |

| designation | yield (%) | melting point °C. (solvent) |
|---|---|---|
| methylamine (c) 6-[N—cyclopentyl-N—(furan-2-ylmethyl)-amino]-2-methyl-amino-9-tetrahydropyran-2-ylpurine from 6-[N—cyclopentyl-N—(furan-2-ylmethyl)-amino]-2-chloro-9-tetrahydropyran-2-ylpurine and methylamine | 72 | oil (dichloromethane) |

Test report

Inhibition of the Liberation of SRS-A (slow reaction substance of anaphylaxis) Caused by Antigen from Guinea Pig Lung Tissue In Vitro.

For the in vitro investigation of the compounds according to the invention, the liberation of SRS-A caused by antigen from passively sensitized lung tissue of guinea pigs was investigated. The investigation was carried out by the following method:

Freshly removed lung tissue which had previously been washed substantially free of blood in situ with Krebs buffer (pH 7.4) was comminuted with a McIlwain tissue chopper, washed with Krebs buffer (pH 7.4) and incubated for 1 hour at ambient temperature with a 1:50 dilution of a homologous anti-ovalbumin (crystallized twice), with the addition of complete Freund's adjuvant, according to the method of G. E. Davies and T. P. Johnstone (Quantitative studies on anaphylaxis in guinea pigs passively sensitized with homologous antibody, Inter. Arch. Allergy, 41, 648–654/1971). Until used, the antiserum was stored undiluted at −18° C.

Subsequently, the passively sensitized tissue was washed twice with Krebs buffer (pH 7.4) and samples each of about 400 mg. incubated in Krebs buffer with and without the addition of test substance (on average $3\times10^{-5}$M) for 30 minutes before the antigen-induced liberation of SRS-A was initiated by the addition of ovalbumin solution (end concentration 10 mg./ml.). The liberation reaction was stopped after 15 minutes by the addition of an equal volume of ice-cold tyrode solution (pH 8.0). After separation of the tissue by centriguing, the supernatants were stored at −18° C. until the measurement of their SRS-A content in the ileum bioassay.

The ileum bioassay was carried out in a partly automated process in superfusion on pieces of ileum from untreated guinea pigs. The working buffer was tyrode solution (pH 8.0) with the addition of atropine ($2\times10^{-7}$M) and mepyramine ($10^{-6}$M).

The superfusion time for the sample was 3 minutes, followed by a rinsing phase of 6 minutes. As a measure for the content of SRS-A content in the sample supernatants increased on average by the factor 3 in comparison with the buffer control.

The substance-caused inhibitory action in percent to the "specific" antigen-induced SRS-A liberation was determined as follows:

$$\frac{(K \text{ liberation with substance}) - (K \text{ buffer control})}{(K \text{ liberation without substance}) - (K \text{ buffer control})}$$

TABLE

Influence of $N^6$-disubstituted adenosine derivatives on the antigen-caused inhibition of the liberation of SRS-A from Guinea pig lung tissue

| | Concentration 20 mM | | Concentration 30 mM | |
|---|---|---|---|---|
| Test compound | number of experiments | inhibition in % of control | number of experiments | inhibition in % of control |
| 2f | 1 | 27 | | |
| 2k | 1 | 38 | | |
| 2o | 1 | 21 | | |
| 6j | | | 3 | 44 |
| 6k | | | 3 | 40 |
| 8g | 4 | 21 | | |
| 8j | 3 | 45 | | |
| 9l | | | 3 | 53 |
| 12a | 3 | 43 | | |

It will be understood that the specification and examples are illustrative but not limitative of the present invention and that other embodiments within the spirit and scope of the invention will suggest themselves to those skilled in the art.

What is claimed is:

1. A compound of the formula:

(I)

wherein $R_1$ and $R_4$ are individually a hydrogen atom, a halogen atom or $NR_6R_7$, $R_6$ and $R_7$ are individually hydrogen, $C_1$–$C_6$ alkyl radical and $R_2$ and $R_3$ are individually alkyl radicals of from 1 to 6 carbon atoms, alkenyl radicals of from 2 to 6 carbon atoms, cycloalkyl radicals of from 3 to 7 carbon atoms, phenylalkyl radicals containing alkyl groups of from 1 to 4 carbon atoms and the phenyl moiety of which is unsubstituted or substituted by halogen, hydroxyl, $C_1$–$C_6$ alkyl, $C_1$–$C_6$ alkoxy, $C_1$–$C_6$ alkylthio or trifluoromethyl, furylmethyl, furylethyl, thiophenemethyl, thiopheneethyl, pyridylmethyl, pyridylethyl, the pyridyl moieties of which are unsubstituted or substituted by $C_1$–$C_4$ alkyl radicals, indanyl or tetrahydronapthyl radicals and $R_5$ is hydrogen, a tetrahydrofuranyl radical, a tetrahydropyranyl radical, or an alkyl radical of from 1 to 10 carbon atoms which is unsubstituted or substituted by hydroxyl, $C_1$–$C_6$ alkanoyloxy, $C_1$–$C_6$ alkoxycarbonyl, $C_2$–$C_6$ carboxyalkanoyloxy, $C_2$–$C_6$ hydroxyalkoxy, $C_3$–$C_6$ dihydroxyalkoxy, carboxyl, cyano or 1H-tetrazol-5-yl radical, or pharmaceutically acceptable salts thereof provided that (i) $R_2$ and $R_3$ are not simultaneously alkyl radicals, or (ii) when $R_5$ is hydrogen, then $R_2$ and $R_3$ are not simultaneously alkenyl, unsubstituted benzyl or furylmethyl, or (iii) when $R_3$ is methyl and $R_5$ is hydrogen, then $R_2$ is not alkenyl, unsubstituted benzyl or furylmethyl.

2. The compound of claim 1, wherein $R_1$ and $R_4$ are the same.

3. The compound of claim 1, wherein $R_1$ and $R_4$ are hydrogen or halogen.

4. The compound of claim 1, wherein $R_1$ or $R_4$ are $N-R_6R_7$.

5. The compound of claim 1, wherein $R_6$ and $R_7$ are selected from the group consisting of hydrogen and alkyl radicals of from 1 to 6 carbon atoms.

6. The compound of claim 5, wherein said alkyl radical is methyl.

7. The compound of claim 1, wherein $R_2$ and $R_3$ are individually 2-propyl, 2-methylpropyl, 3-pentyl, allyl, cyclopentyl, cyclohexyl or indanyl radical or a benzyl radical optionally substituted one or more times by chlorine, fluorine, methyl, triflouromethyl or methoxy; a furylmethyl, thiophenemethyl, thiopheneethyl group or a pyridinemethyl radical optionally substituted by methyl.

8. The compound of claim 1, wherein $R_5$ is hydrogen, tetrahydrofuran-2-yl, tetrahydropyran-2-yl, 2-hydroxypropyl, 2,3-dihydroxypropyl, 2-acetoxypropyl, 2-succinoyloxypropyl, (2-hydroxyethoxy)-methyl, 1-(1,3-dihydroxy-2-propoxy)-2-hydroxyethyl, 8-methoxycarbonyloctyl, 8-carboxyoctyl, 4-cyanobutyl or 4-(1H-tetrazol-5-yl)-butyl radical.

9. The compound of claim 1, designated 6-(N-benzyl-N-cyclopentylamino)-9-tetrahydrofuran-2-yl-purine or pharmaceutically acceptable salts thereof.

10. The compound of claim 1, designated 6-[N-cyclopentyl-N-(2,5-dimethylbenzyl)-amino]-9-tetrahydropyran-2-yl-purine or pharmaceutically acceptable salts thereof.

11. The compound of claim 1, designated 6-[N-indan-1-yl)-N-(2-methylpropyl)-amino]-9-tetrahydropyran-2-yl-purine or pharmaceutically acceptable salts thereof.

12. The compound of claim 1, designated 6-[N-cyclopentyl-N-(thiophen-2-yl methyl)-amino]-purine or pharmaceutically acceptable salts thereof.

13. The compound of claim 1, designated 6-[N-cyclopentyl-N-(4-methoxybenzyl)-amino]-purine or pharmaceutically acceptable salts thereof.

14. The compound of claim 1, designated 6-(N-allyl-N-cyclohexylamino)-2-methylaminopurine or pharmaceutically acceptable salts thereof.

15. The compound of claim 1, designated 6-(N-allyl-N-cyclohexylamino)-purine or pharmaceutically acceptable salts thereof.

16. The compound of claim 1, designated 6-[N-cyclopentyl-N-(6-methylpyridin-2-ylmethyl)-amino]-purine or pharmaceutically acceptable salts thereof.

17. The compound of claim 1, designated 6-[N-cyclopentyl-N-(2,5-dimethylbenzyl)-amino]-9-tetrahydrofuran-2-yl-purine or pharmaceutically acceptable salts thereof.

18. The compound of claim 1, designated 6-[N-cyclopentyl-N-(2,5-dimethyl benzyl)-amino]-9-(2,3-dihydroxypropyl)-purine or pharmaceutically acceptable salts thereof.

19. The compound of claim 1, designated 6-[N-(-chloro-2-methoxybenzyl)-N-cyclopentylamino]-9-(2,3-dihydroxypropyl)-purine or pharmaceutically acceptable salts thereof.

20. The composition useful in treating allergic diseases, bronchospastic and bronchoconstrictory conditions, comprising a therapeutically effective amount of the compound of claim 1, in a pharmaceutically acceptable carrier.

21. The composition of claim 20, wherein said compound is selected from the group consisting of 6-[N-cyclopentyl-N-(2,5-dimethylbenzyl)-amino]-9-tetrahydropyran-2-yl-purine, 6-[N-(indan-1-yl)-N-(2-methylpropyl)-amino]-9-tetrahydropyran-2-yl-purine, 6-[N-benzyl-N-cyclopentylamino)-9-tetrahydrofuran-2-yl-purine, 6-[N-cyclopentyl-N-(thiophen-2-yl methyl)-amino]-purine, 6-cyclopentyl-N-(4-methoxybenzyl)-amino]-purine, 6-N-allyl-N-cyclohexylamino)-2-methylaminopurine, 6-(N-allyl-N-cycloyhexylamino)-purine, 6-[N-cyclopentyl-N-(6-methyl pyridin-2-ylmethyl)-amino]-purine, 6-[N-cyclopentyl-N-(2,5-dimethylbenzyl)-amino]-9-tetrahydrofuran-2-yl-purine, 6-[N-cyclopentyl-N-(2,5-dimethyl benzyl)-amino]-9-(2,3-dihydroxypropyl)-purine, 6-[N-(5-chloro-2-methoxybenzyl)-N-cyclopentylamino]-9-(2,3-dihydroxypropyl)-purine pharmaceutically acceptable salts of said compounds.

22. A method of treating allergic diseases, bronchospastic and bronchoconstrictory conditions, comprising administering to a subject a therapeutically effective amount of the compound of claim 1 in a pharmaceutically acceptable carrier.

23. A method of claim 22, wherein said compound is administered in an amount ranging from about 0.1 to about 50 mg/kg of body weight of said subject per day of treatment.

24. A method as in claim 22, wherein said compound is a administered in an amount ranging from about 0.5 to 40 mg/kg of body weight of said subject per day of treatment.

25. A method as in claim 22, wherein said compound is administered in an amount ranging from about 1.0 to about 10 mg/kg of body weight of said subject per day of treatment.

26. A method as claim 22, wherein said compound is selected from the group consisting of 6-[N-cyclopentyl-N-(2,5-dimethylbenzyl)-amino]-9-tetrahydropyran-2-yl-purine, 6-[N-(indan-1-yl)-N-(methylpropyl)-amino]-9-tetrahydropyran-2-yl-purine, 6-[N-benzyl-N-cyclopentyl-amino)-9-tetrahydrofuran-2-yl-purine, 6-[N-cyclopentyl-N-(thiophen-2-yl methyl)-amino]-purine, 6-cyclopentyl-N-(4-methoxybenzyl)-amino]-purine, 6-N-allyl-N-cyclohexylamino)-2-methylaminopurine, 6-(N-allyl-N-cycloyhexylamino)-purine, 6-[N-cyclopentyl-N-(6-methyl-pyridin-2-ylmethyl)-amino]-purine, 6-[N-cyclopentyl-N-(2,5-dimethylbenzyl)-amino]-9-tetrahydrofuran-2-yl-purine, 6-[N-cyclopentyl-N-(2,5-dimethyl benzyl)-amino]-9-(2,3-dihydroxypropyl)-purine, 6-[N-(5-chloro-2-methoxybenzyl)-N-cyclopentylamino]-9-(2,3-dihydroxypropyl)-purine, or a pharmaceutically acceptable salts of said compounds.

* * * * *

UNITED STATES PATENT AND TRADEMARK OFFICE
CERTIFICATE OF CORRECTION

PATENT NO. : 4,853,386  
DATED : August 1, 1989  
INVENTOR(S) : Walter-Gunar Friebe, et al.

It is certified that error appears in the above-identified patent and that said Letters Patent is hereby corrected as shown below:

| | |
|---|---|
| Col. 2, line 5: | change "tetrahydrofurn" to -- tetrahydrofuran --. |
| Col. 2, line 9: | change "methoxycarbonylcoctyl" to -- methoxycarbonyloctyl --. |
| Col. 4, line 17: | change "6-[Benzyl" to -- 6-[N-Benzyl --. |
| Col. 4, line 22: | change "N-benzyl---methylpropylamine" to -- N-benzyl-2-methylpropylamine --. |
| Col. 6, line 17: | entry "u" change "amino]-tetrahydropyran" to --amino]-9-tetrahydropyran --. |
| Col. 7, line 63: | change "3.5 g (mmol)" to -- 3.5 g (9 mmol) --. |
| Col. 9, line 23: | change "methylpropyl-amino]-amino-]purine" to -- methylpropyl)-amino]-purine --. |
| Col. 9, line 27: | change "1,3-dioxalan" to -- 1,3-dioxolan --. |
| Col. 11, line 9: | change ")36%" to (36% --. |
| Col. 14, line 12: | change "20" to -- 2o --. (in Table - test compound) |
| Col. 14, line 44: | change "1 to$_4$" to -- 1 to 4 --. |

UNITED STATES PATENT AND TRADEMARK OFFICE
CERTIFICATE OF CORRECTION

PATENT NO. : 4,853,386

DATED : August 1, 1989

INVENTOR(S) : Walter-Gunar Friebe, et al.

It is certified that error appears in the above-identified patent and that said Letters Patent is hereby corrected as shown below:

Col. 16, line 1: change "6-[N-chloro" to -- 6-[N-(5-chloro --.

Col. 16, line 18: change "6-N-allyl" to -- 6-(N-allyl --.

Abstract (line 21): change "$C_3-C_6$" to -- $C_3-C_6$ --.

Col. 16, line 17: change " 6-cyclopentyl-" to --6-[N-cyclopentyl- --.

Signed and Sealed this

Thirty-first Day of July, 1990

Attest:

HARRY F. MANBECK, JR.

*Attesting Officer*      *Commissioner of Patents and Trademarks*